United States Patent
Arumugam et al.

(10) Patent No.: US 9,915,675 B2
(45) Date of Patent: Mar. 13, 2018

(54) METHODS AND APPARATUS FOR DETERMINING ASPIRATION AND/OR DISPENSING VOLUME AND/OR PIPETTE POSITIONING

(71) Applicant: Siemens Healthcare Diagnostics Inc., Tarrytown, NY (US)

(72) Inventors: Bharath K. Arumugam, Mahwah, NJ (US); Domenico Menafra, Northvale, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/034,442

(22) PCT Filed: Oct. 30, 2014

(86) PCT No.: PCT/US2014/063186
§ 371 (c)(1),
(2) Date: May 4, 2016

(87) PCT Pub. No.: WO2015/066342
PCT Pub. Date: May 7, 2015

(65) Prior Publication Data
US 2016/0291049 A1   Oct. 6, 2016

Related U.S. Application Data

(60) Provisional application No. 61/899,424, filed on Nov. 4, 2013.

(51) Int. Cl.
*B01L 3/02* (2006.01)
*G01N 35/00* (2006.01)
(Continued)

(52) U.S. Cl.
CPC .......... *G01N 35/1016* (2013.01); *B01L 3/022* (2013.01); *G01F 23/292* (2013.01);
(Continued)

(58) Field of Classification Search
CPC .. A61M 2205/3306; A61M 2205/3389; A61M 5/31568; B65B 3/003; B65B 3/30;
(Continued)

(56) References Cited

U.S. PATENT DOCUMENTS 6,599,476 B1 * 7/2003 Watson ............... B65G 47/1471
141/1
7,982,201 B2 * 7/2011 Bryant ................. G01F 23/292
250/577
(Continued)

FOREIGN PATENT DOCUMENTS

WO    2012/100235 A2    7/2012

OTHER PUBLICATIONS

PCT International Search Report and Written Opinion dated Feb. 23, 2015 (8 pages).
(Continued)

*Primary Examiner* — Jennifer Wecker (57) ABSTRACT

Methods of determining or verifying proper operation of a diagnostic device are disclosed. The methods include monitoring, with one or more image capture devices, one or more locations to determine proper aspiration, dispense, and/or overall assay component volume fill of one or more bio-liquid containers. Tip immersion depth and location may be also measured and/or verified. Diagnostic devices and apparatus adapted to carry out the method are described, as are other aspects.

21 Claims, 6 Drawing Sheets

(51) Int. Cl.
*G01N 35/10* (2006.01)
*G01F 23/00* (2006.01)
*G01F 23/292* (2006.01)
*A61M 5/31* (2006.01)
*G06T 7/00* (2017.01)
*A61M 5/315* (2006.01)
*G01B 11/00* (2006.01)

(52) U.S. Cl.
CPC ... *G01N 35/0099* (2013.01); *G01N 35/00732* (2013.01); *G01N 35/1011* (2013.01); *A61M 5/31568* (2013.01); *A61M 2205/3306* (2013.01); *A61M 2205/3389* (2013.01); *B01L 2200/143* (2013.01); *B01L 2400/0478* (2013.01); *G01B 11/00* (2013.01)

(58) Field of Classification Search
CPC .............. G01B 11/00; G01F 23/292; G06T 2207/30004; G06T 7/602
See application file for complete search history.

(56) References Cited

U.S. PATENT DOCUMENTS

| | | | | |
|---|---|---|---|---|
| 2005/0045653 | A1* | 3/2005 | Tanaka | B05B 15/08 222/1 |
| 2006/0151727 | A1* | 7/2006 | Kamiya | G02F 1/1341 250/577 |
| 2006/0178578 | A1* | 8/2006 | Tribble | B65B 3/003 600/432 |
| 2006/0238346 | A1* | 10/2006 | Teller | B67D 3/0077 340/572.1 |
| 2007/0107801 | A1* | 5/2007 | Cochran | B65B 3/36 141/153 |
| 2008/0169044 | A1 | 7/2008 | Osborne et al. | |
| 2009/0188311 | A1* | 7/2009 | Cadieux | A61M 5/14546 73/149 |
| 2009/0198208 | A1* | 8/2009 | Stavsky | A61J 1/2096 604/407 |
| 2010/0066996 | A1* | 3/2010 | Kosaka | G01F 23/292 356/39 |
| 2011/0056290 | A1* | 3/2011 | Bryant | G01F 23/292 73/293 |
| 2013/0065797 | A1 | 3/2013 | Silbert et al. | |
| 2013/0280143 | A1* | 10/2013 | Zucchelli | B25J 9/1697 422/501 |
| 2014/0025199 | A1* | 1/2014 | Berg | G07F 11/005 700/232 |

OTHER PUBLICATIONS

Extended EP Search Report dated Oct. 7, 2016 of corresponding European Application No. 14858935.1, 4 Pages.

* cited by examiner

METHODS AND APPARATUS FOR DETERMINING ASPIRATION AND/OR DISPENSING VOLUME AND/OR PIPETTE POSITIONING

RELATED APPLICATION

This application claims priority to U.S. Provisional Application Ser. No. 61/899,424 entitled "METHODS AND APPARATUS FOR DETERMINING ASPIRATION AND/OR DISPENSING VOLUME AND/OR PIPETTE POSITIONING" filed on Nov. 4, 2013, the disclosure of which is hereby incorporated by reference in its entirety herein.

FIELD

The present invention relates generally to diagnostic instruments and methods of operation thereof.

BACKGROUND

A wide variety of automated diagnostic instruments (e.g., chemical analyzers or immunoassay instruments) are used to analyze patient specimens. These diagnostic instruments may conduct assays or testing using one or more reagent or other additions to identify one or more analytes in, or characteristics of, a biological liquid such as urine, blood serum or plasma, cerebrospinal liquids, and the like (hereinafter "bio-liquid"). For convenience and safety reasons, these bio-liquids may be contained within sample containers (e.g., sample tubes).

For certain tests, the patient specimen may include a serum or plasma portion (obtained from whole blood by centrifugation). To prevent clotting, an anticoagulant such as citrate or heparin may be added to the patient specimen. After centrifuging and subsequent de-capping, the open sample container (e.g., sample tube) may be transported to, or otherwise reside in, a support article, such as a sample rack.

The sample rack may be accessible by a pipette of an aspirating system that may extract bio-liquid from the sample container and combine the bio-liquid with one or more reagents and possibly a diluent in a reaction container (e.g., cuvette or cup). After incubation or reaction, analytical measurements may then be performed, using, for example, photometric or fluorometric readings, or the like. The measurements allow determination of values from which an amount of analyte or other substance related to the health of the patient may be determined using well-known techniques.

In some cases, improper addition of amounts of specimen, other liquids, and/or liquid or solid reagents may affect the integrity of the testing results, such as the analyte reading of a clinical analyzer. Verification of the aspiration amount of the patient specimen may have been accomplished by recording and monitoring aspiration pressure readings in prior systems. However, this method may be problematic in some instances, especially at low volumes. Verification of liquid reagent addition and diluent may suffer from similar problems. Solid reagent addition may not be verified using existing methods.

Because of the problems encountered due to improper addition amounts of specimen, reagent, and/or liquid or diluent addition, there is an unmet need for methods and apparatus adapted to measure and/or verify such additions in clinical testing.

SUMMARY

According to a first embodiment, a method of determining an aspiration and/or dispense is provided. The method includes providing a bio-liquid container, either aspirating from or dispensing to the bio-liquid container, and capturing one or more images of the bio-liquid container indicative of the aspirating and/or dispensing.

According to another embodiment, a transfer apparatus is provided. The transfer apparatus includes a support article adapted to receive a bio-liquid container, and an image capture apparatus located adjacent to the support article and operable to capture two or more images of the bio-liquid container before, during, or after either of an aspiration or a dispense.

According to another embodiment, a diagnostic device is provided. The diagnostic device includes a transfer apparatus including a first support article adapted to receive a first bio-liquid container, a second support article adapted to receive a second bio-liquid container, an image capture apparatus located adjacent to one or more of: the first support article and operable to capture one or more images of the bio-liquid container at one or more points in time during a bio-liquid aspiration, the second support article and operable to capture one or more images of the second bio-liquid container at one or more points in time during a bio-liquid dispense, the second support article and operable to capture one or more images of the second bio-liquid container at one or more points in time during a reagent dispense, and the second support article and operable to capture one or more images of the second bio-liquid container after all subcomponent additions, and an image processor operable to process the images to determine at least one selected from a group of: an aspiration height or aspiration volume, a dispense height or dispense volume, an overall height or volume addition, a tip insertion depth, and combinations thereof.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

Accurate measurement of the correct volume of liquids and other assay components (e.g., aspiration and/or dispense volume) is desirable in laboratory diagnostic instruments (e.g., clinical analyzers and immunoassay instruments). In particular, it is desirable that additions of amounts of liquid reagent, solid or semisolid reagents, specimen, and diluent (hereinafter "assay subcomponents") be relatively tightly controlled. For example, a pipetting operation can be one component of a laboratory diagnostics instrument. Substantial errors in assay results may be due to incorrect aspiration and/or dispensing of an amount (volume) of specimen, liquid, semisolid or solid reagent, or even diluent. In one case, an accuracy of liquid aspirated/dispensed by a pipetting operation may be influenced by any number of factors, such as properties of the aspirated or dispensed liquid, environment, temperature, and humidity. In some cases, even a minor error in measurement of aspirated and/or dispensed volume can have a substantial or strong influence on the accuracy of the test result (e.g., assay result).

In a first broad aspect, embodiments of the present invention provide methods and apparatus to measure and/or verify aspiration and/or dispensed amounts of the specimen, one or more reagents, diluent, and other liquids used in diagnostic instruments. The method may provide a non-invasive amount measurement and/or verification. In particular, one or more embodiments include an image capture device, such as an on-board digital camera, mounted within the diagnostics instrument. The image capture device can be used to capture one or more images and/or videos of a bio-liquid container (such as a blood collection tube or cuvette), or other actions of components (e.g., a pipette) of a liquid transfer apparatus used in the diagnostic instrument. The captured images can be processed by a computing algorithm of an image processor to determine and/or verify various height and/or volume changes due to the aspiration or dispensing of various assay components. Accordingly, the transfer apparatus may verify the accuracy of the dispensed specimen, diluent liquid, reagent, final volume, right mix of reagents, or the like.

The action recorded (e.g., captured images) by the image capture device and processed by the image processor can determine, in some embodiments, if a standard operating procedure has been properly carried out. For example, fault detection in the execution of pipetting actions, such as immersion and immersion depth of the pipette, aspiration volume, dispense volume, or the like may be carried out. Even sporadic, hard-to-catch errors can be captured by processing one or more images/videos captured by the image capture device. Furthermore, these captured images and/or videos can be archived in a suitable memory to serve as undeniable proof that a correct operating procedure was followed for a particular test.

According to one or more embodiments, an image capture device, such as an on-board camera (e.g., digital camera or the like) can be used for capturing one or more images at times during an aspiration, such as: before commencing aspiration, during aspiration, and/or after aspiration. In some embodiments, an image taken before aspiration can be used for determining the quality and consistency of a pipette or carrying vessel (cuvette). For example, a flaw in the pipette or pipette tip may be determined. Analyzing the captured image of the container vessel further ensures result accuracy.

In some embodiments, an image taken during aspiration can be used for tip immersion depth analysis. Increased immersion depth may result in additional liquid or even red blood cells or coagulant being drawn into the pipette. Decreased immersion depth may result in air bubbles. Additionally, gross increases in immersion depth may result in the pipette touching the sample container bottom and effectively reduce the aspirated volume. All of this information can be processed by the image processor using the details provided by the images captured by an image capture device, such as an on-board camera.

In one or more embodiments, an image taken after aspiration can be used to determine a volume of liquid that has been aspirated. This may be accomplished by comparing a liquid height within the bio-liquid container before and after the aspiration, possibly coupled with determining a size of the bio-liquid container, if different sized containers are used. Furthermore, the captured images can be used for analyzing a color of the aspirated liquid, and measuring a height location of an upper or lower meniscus in the bio-liquid container as desired. The ability to measure and/or verify the proper volume (aspiration and/or dispense) may improve an accuracy of the assay result.

These and other aspects and features of embodiments of the invention will be described with reference to FIGS. 1-8 herein.

Figure 1:
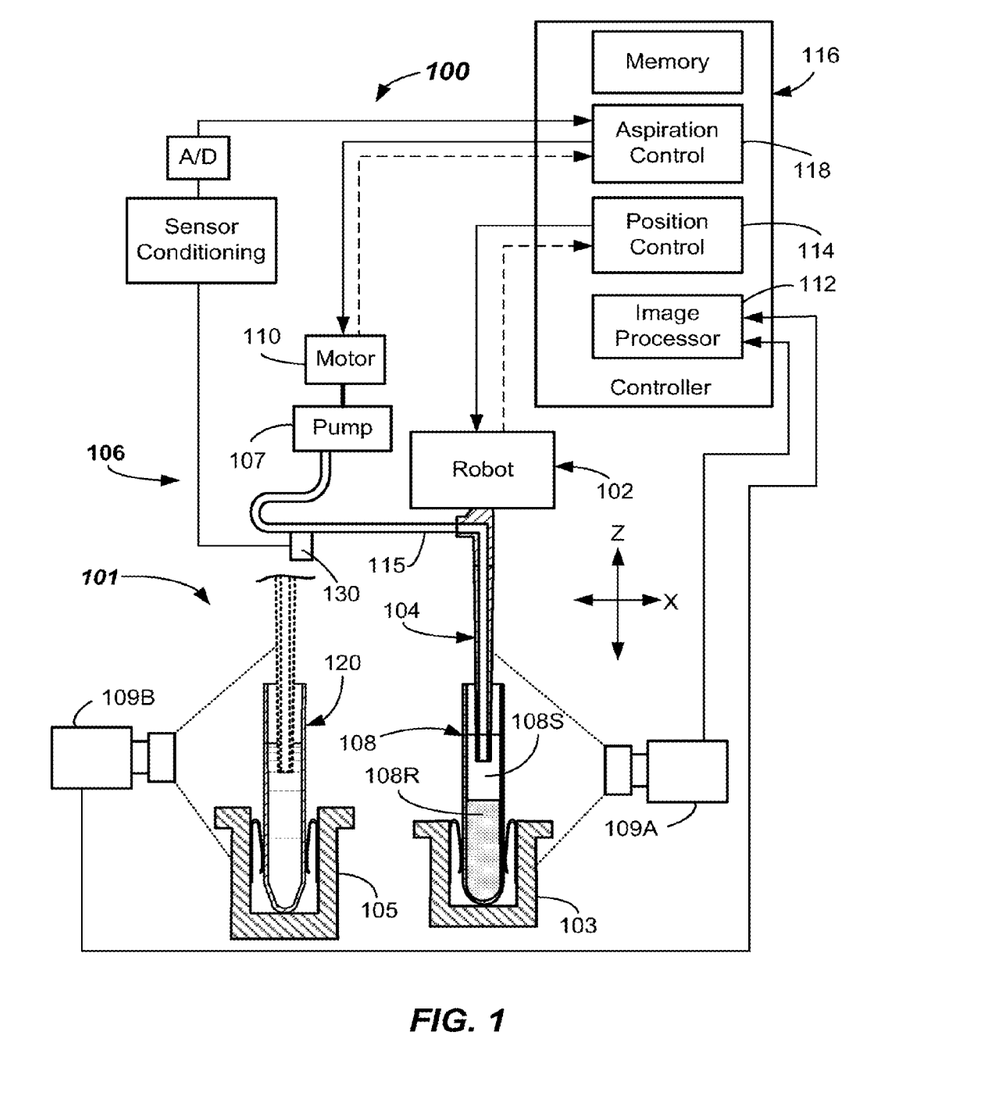
FIG. 1 illustrates a schematic side view of a diagnostic device including a liquid transfer apparatus according to embodiments.

FIG. 1 illustrates a diagnostic device 100 including a transfer apparatus 101, which in one aspect is capable of automatically determining a characteristic of a first bio-liquid container 108 (e.g., test tube or blood collection tube—see FIG. 1) such as a diameter and/or height thereof, and/or a characteristic of a bio-liquid specimen 108S contained therein, and in particular, a change in amount (e.g., height or volume) contained in the first bio-liquid container 108 before and after aspiration. The transfer apparatus 101 may be capable of measuring and/or verifying a height or volume of a liquid, solid, or semisolid reagent, diluent, and/or specimen, or combination thereof that is contained in a second bio-liquid container 120, for example. This may be performed prior to analytical analysis by the diagnostic device 100, which may be carried out by any suitable conventional testing device in the diagnostic device 100, such as a luminometer, fluoroscope, absorbance device, or the like (not shown). The first and second bio-liquid containers 108, 120 may be any generally clear, transparent, translucent or other suitable container may be used, such as a sample cup, cuvette, or other clear glass or plastic container. In one or more embodiments, the first bio-liquid container 108 is a blood collection tube, and the second bio-liquid container 120 is a cuvette.

Again referring to FIG. 1, the diagnostic device 100 includes a first support article 103, such as a sample rack that is adapted to receive the first bio-liquid container 108 containing a bio-liquid specimen 108S and possibly another material, such as a red blood cell (RBC) portion 108R. A second support article 105, such as an incubation member (e.g., incubation ring) may be configured and adapted to receive the second bio-liquid container 120 (e.g., a cuvette). An image capture apparatus may be positioned adjacent to one or more of the components of the diagnostic device 100 (e.g., at the sides thereof). For example, a first image capture device 109A may be located adjacent to the first support article 103 (e.g., at a side thereof). A second image capture device 109B may be located adjacent to the second support article 105 (e.g., at a side thereof). The location of the first support article 103 and the second support article 105 may be at aspiration and dispense stations, respectively. Other image capture devices may be positioned and focused on other areas within the diagnostic device 100.

The image capture devices (e.g., 109A, 109B) described herein may be a suitable digital camera. A suitable digital camera is a model Dragonfly2 (DR2) available from Point Grey Research. Other digital cameras or types of image capture devices may be used. An image processor 112 may receive the one or more captured images from the image capture devices 109A, 109B and process the images according to a processing scheme or algorithm. The image processor 112 may be any suitable computing device that is capable of performing an analysis of the captured digital images. For example, the image processor 112 may be a computer having a suitable processor such as a microprocessor-based central processing unit (CPU) and memory and may perform an analysis of an aspiration of the bio-liquid specimen 108S in the first bio-liquid container 108 as it resides in the first support article 103. The image processor 112 is adapted to analyze the two or more images in some embodiments. The two or more images may be sequentially obtained and analyzed to obtain a change in volume, as will be apparent from the following. An illumination source (not shown) may be used to locally illuminate the first bio-liquid container 108 at times during the aspiration. The illumination source may be one or more LED lights, for example. Other types of lighting may be used. Similar lighting may be provided at the second support article 105.

Again referring to FIG. 1, the transfer apparatus 101 may include an aspiration apparatus 106 as illustrated. The aspiration apparatus 106 may include any suitable robot 102 and a pipette 104 (sometimes referred to as a sample probe) adapted to aspirate the bio-liquid specimen 108S. Bio-liquid specimen 108S may also be dispensed by the aspiration apparatus 106. The robot 102 may be configured and adapted to carry out motion of the pipette 104 in one or more coordinate directions, such as X, Y (into and out of the paper), and/or Z. However, typically, the robot 102 may move the pipette 104 in the X and Z directions only.

The robot 102 may be any suitable robot adapted to move the pipette 104, and may include one or more robot components (e.g., robot arm(s), link(s), boom(s), frame (s), or the like) to which the pipette 104 may be mounted to accomplish motion thereof. The robot 102 may be operable to descend and ascend the pipette 104 into and out of the first bio-liquid container 108 containing a bio-liquid specimen 108S, so that at least some may be aspirated. The bio-liquid specimen 108S may be blood serum, plasma, cerebral liquid, spinal liquid, interstitial liquid, urine, or the like. Other liquids may be aspirated. The robot 102 may be suitably actuated under the control of a position control 114 of a controller 116 to impart the desired motions to the pipette 104 in one dimension, two dimensions, or three dimensions.

For example, the robot 102 may be operated by signals from the position control 114 to move the pipette 104 from the first bio-liquid container 108 to the second bio-liquid container 120, such as a reaction vessel (e.g., a cuvette). The aspirator apparatus 106 may be provided to aspirate a desired amount of bio-liquid specimen 108S into the interior of the pipette 104.

The aspirator apparatus 106 may include a pump 107 that may include a pumping chamber (not shown). For example, pump 107 may be a piston-type pump that may be driven by a suitable motor 110, such as a stepper motor. Other types of pumps may be used. The pump 107 may be adapted to cause a liquid (e.g., a bio-liquid specimen 108S) to aspirate into the interior of the pipette 104. The aspiration takes place via operation of the pump 107, which creates an internal pressure to cause flow and aspiration of the bio-liquid specimen 108S. The pump 107 may operate on a backing liquid (e.g., water) contained within a main supply line 115. Main supply line 115 may include a flexible tube section along most of its length in some embodiments. Flexible tube section may be a section of hollow Teflon tube or other suitably flexible conduit. An aspiration pressure may be verified by sensor 130.

The pump 107 may be configured to have excellent precision at low volume aspiration and dispensing (e.g., less than 25 µL). In the depicted aspiration apparatus 106, when operated in a low-volume aspiration mode, a total aspirated volume per aspiration cycle may be about 25 µL or less, or even about 20 µL or less, or even about 15 µL or less, or even about 10 µL or less in some embodiments. It should be recognized that the aspiration apparatus 106 may capable of discrimination at higher aspiration volumes, as well (e.g., greater than 30 µL).

Aspiration control 118 of the controller 116 may be adapted and operational to control the motor 110, and thus the pump 107 to draw in (e.g., aspirate) a desired amount of the bio-liquid specimen 108S into the interior of the pipette 104. Aspiration control 118 of the controller 116 may also control the dispensing operations performed by the aspiration apparatus 106. The aspiration apparatus 106 may include other conventional components, such as one or more valve(s), accumulator(s), distributors, sensors, or other hydraulic components (not shown) to effectuate the liquid aspiration. Any suitable apparatus for aspirating the liquid into the pipette 104 may be used. For example, aspirating and dispensing systems, which may be used with the present invention, are described in U.S. Pat. Nos. 7,867,769; 7,634,378; 7,477,997; 7,186,378; 7,150,190; and 6,370,942.

Figure 5:
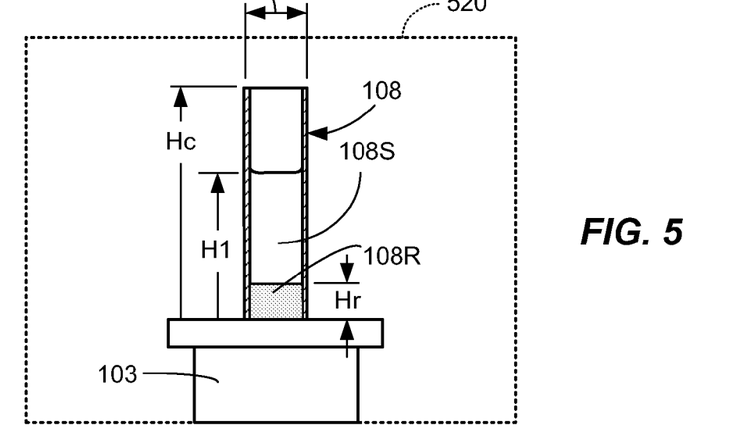
FIGS. 5-7 illustrate various captured images before, during, and after aspiration according to embodiments.
Figure 6:
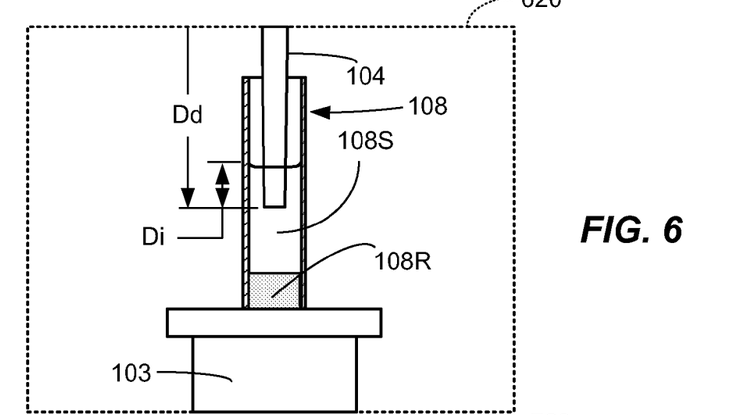

Operation of the image capture devices 109A, 109B and image processor 112 will now be described. In one or more embodiments, the first image capture device 109A is focused and operable to capture one or more images of the bio-liquid container 108 at one or more points in time during the bio-liquid aspiration. In particular, images may be captured before aspiration, as shown in FIG. 5, during aspiration as shown in FIG. 6, or after aspiration, as in FIG. 7. The image processor 112 may be operable to process the various captured images to determine various physical dimension aspects of the bio-liquid specimen 108S, and RBC portion 108R (if present) and/or pipette 104. For example, a first captured image 520 that has been captured with the image capture device 109A may be analyzed and processed by the image processor 112 to determine a container height (Hc) and/or container diameter (Dc) of the bio-liquid container 108. In another aspect, the first captured image 520 may be analyzed and processed to obtain an initial height (H1) of the top-most meniscus portion of the bio-liquid specimen 108S from a datum, such as a top of the first support article 103 before aspiration takes place. From this, an initial aspiration volume (V1) may be determined. If a second component of the specimen is present, such as a RBC portion 108R, the uppermost height (Hr) of the RBC portion 108R may also be determined.

As shown in FIG. 6, a second image 620 may be captured with the image capture device 109A at a point when the pipette 104 is immersed in the bio-liquid specimen 108S and ready to aspirate. This image may be processed by the image processor 112 to determine and/or verify a depth of insertion (Di) and test that determined depth against one or more threshold depths in memory. By knowing the initial height (H1) of the top-most portion of the bio-liquid specimen 108S from the previous image capture, proper pipette insertion depth (Dd) from a start point above the bio-liquid container 108 of the pipette 104 by the position control 114 ensured. Further, each respective image that is captured by the image capture device 109A may be saved in memory as an archive. Additionally, each respective image that is captured by the image capture device 109A may be correlated with stored images in memory to determine any anomalies of the pipette 104, such as a damaged tip of the pipette 104, improper tip alignment, improper start position for tip, improper location of the bio-liquid container 108 in the first support article 103, or the like.

Figure 7:
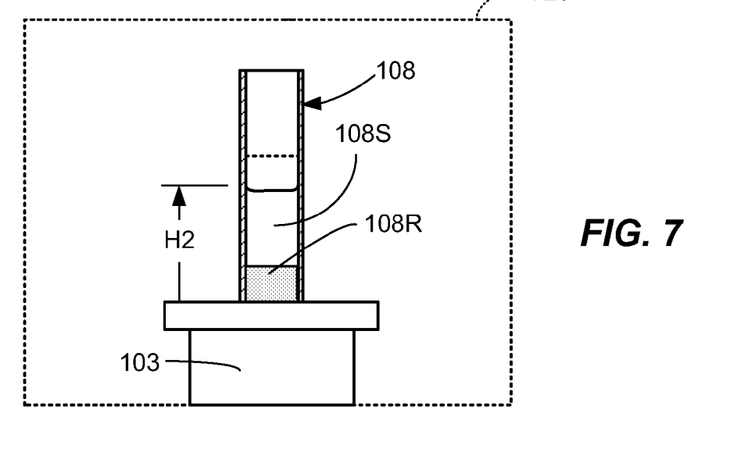

After aspiration has taken place, the pipette 104 may be withdrawn from the bio-liquid container 108, and a third captured image 720 may be obtained with the capture device 109A. This third captured image 720 may be analyzed and processed by the image processor 112 to obtain an after-aspiration height (H2) of the top-most liquid meniscus from the datum, such as a top of the first support article 103. A height change difference (delta H) between H1 and H2, or a volume change calculated by using delta H and Dc may be used to measure and/or verify the aspiration. This verification may be in addition to, or in replacement of, a verification that may be provided by monitoring aspiration pressure with a sensor 130 during the aspiration.

Similar to the discussion above, the second support article 105 (e.g., an incubation ring) containing the second bi-liquid container 120 (e.g., a cuvette) may be imaged by an image capture device 109B. Other types of second bio-liquid containers 120 may be used, such as cups, wells and the like. Image capture device 109B may be the same type of digital camera as discussed for Image capture device 109A. Image capture device 109B may be operable to capture one or more images of the second bio-liquid container 120 at one or more points in time during a bio-liquid dispense. For example, as in the aspiration, two or more images captured before, during, or after dispense may be captured. The differential heights measurements may be used alone, or may be used to determine the dispensed volume and/or to verify proper dispense. In another aspect, an image may be analyzed by the image processor 112 and used to verify that a second bio-liquid container 120 (e.g., cuvette) is indeed present in the receptacle of the second support article 105 (e.g., incubation ring). Insertion depth of the pipette 104 in the second bio-liquid container 120 may also be set and/or verified.

Figure 2:
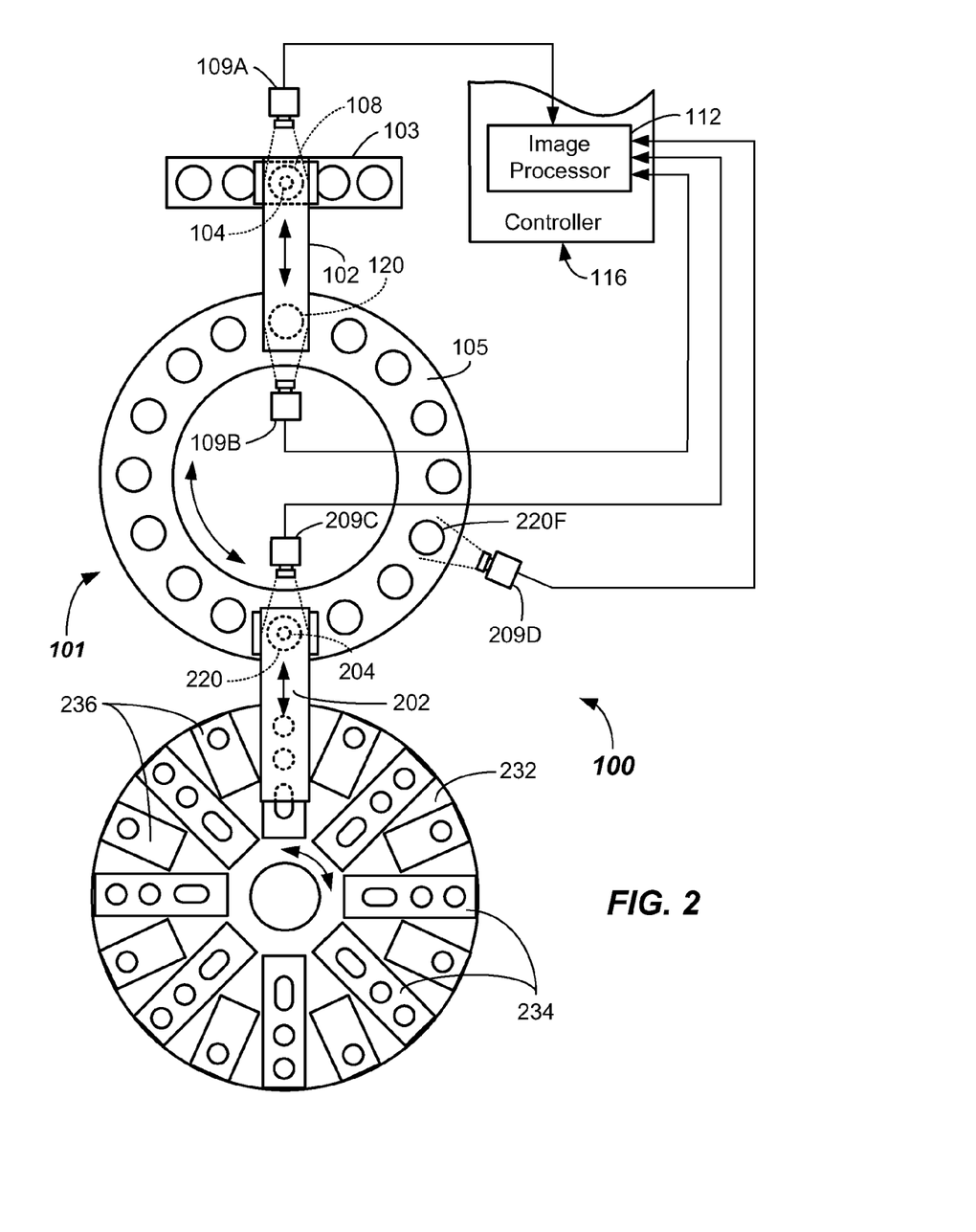
FIG. 2 illustrates a schematic top plan view of a diagnostic device including a liquid transfer apparatus according to embodiments.

FIG. 2 illustrates a top view of some components of a diagnostic device 100 with conventional components not shown such as a test reader (e.g., luminometer), cuvette loader, tip storage, motors, and the like. The diagnostic device 100 including the transfer apparatus 101 includes the first image capture device 109A located adjacent to a side of the first support article 103 (e.g., a five-position sample rack), second image capture device 109B located adjacent to a side of the second support article 105 (e.g., an inside of an incubation ring), and robot 102 adapted to move the pipette 104 (shown dotted) along the direction of arrow.

Also included in the diagnostic device 100 may be a reagent support 232, such as a carousel, adapted to support one or more reagent containers containing one or more reagents, such as primary reagent containers 234 and ancillary reagent containers 236. Other reagent containers may be provided elsewhere. Another image capture device 209C may be positioned adjacent to the second support article 105 and may be operable to capture one or more images of a bio-liquid container 220 (shown dotted) at one or more points in time during a reagent dispense. During the reagent dispense, a pipette 204 (shown dotted) moveable by a second robot 202 may dispense one or more reagents from the primary reagent containers 234 and/or ancillary reagent containers 236. One second robot 202 and coupled pipette 204 is shown. However, multiple robots and coupled pipettes may be used for the various reagent additions. As before, the image capture device 209C may capture one or more images of the bio-liquid container 220 before, during, or after reagent addition. Thus, a change in height of the liquid in the bio-liquid container 220 before, during, and after reagent addition may be determined. Accordingly, reagent amount (e.g., height and/or volume) addition may be measured and/or verified. If multiple reagent additions occur, then each addition may be measured and/or verified with image capture device 209C. Tip insertion depth may also be measured and/or verified, as discussed above.

In another broad aspect, an image capture device 209D may be positioned adjacent to the second support article 105 and may be operable to capture one or more images of a second bio-liquid container 220F after completion of all assay subcomponent additions (e.g., specimen, one or more reagents, and possibly a diluent). Accordingly, a measurement of and/or verification of an overall height or volume addition of the assay subcomponents may be accomplished.

Figure 3:
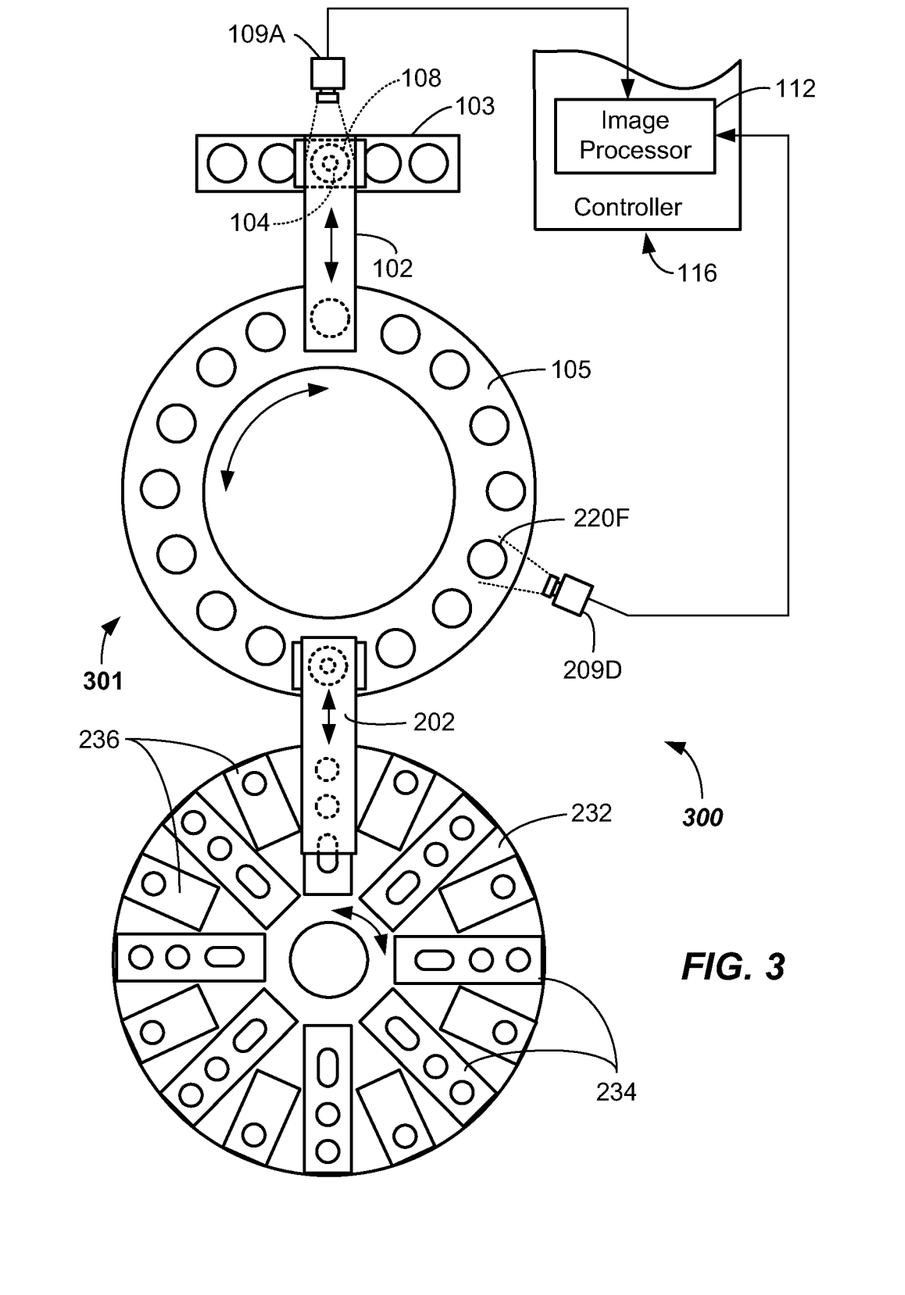
FIG. 3 illustrates a schematic top plan view of a diagnostic device including an alternative liquid transfer apparatus according to embodiments.

Various diagnostic devices including various collections and combinations of image capture devices (e.g., 109A, 109B, 209C, 209D) may be provided in accordance with embodiments of the invention. For example, as shown in FIG. 3, a diagnostic device 300 including a transfer apparatus 301 may include a first image capture device 109A located adjacent to a side of the first support article 103 (e.g., sample rack) as previously described, and at another location, such as adjacent to the second support article 105 (e.g., incubation ring), a second image capture device 209D may be provided. The first image capture device 109A may allow for measurement of and/or verification of an overall height or volume aspiration of the bio-liquid specimen 108S. The second image capture device 209D may allow for measurement of and/or verification of an overall height or volume addition of all the assay subcomponents in the second bio-liquid container 220F.

Figure 4:
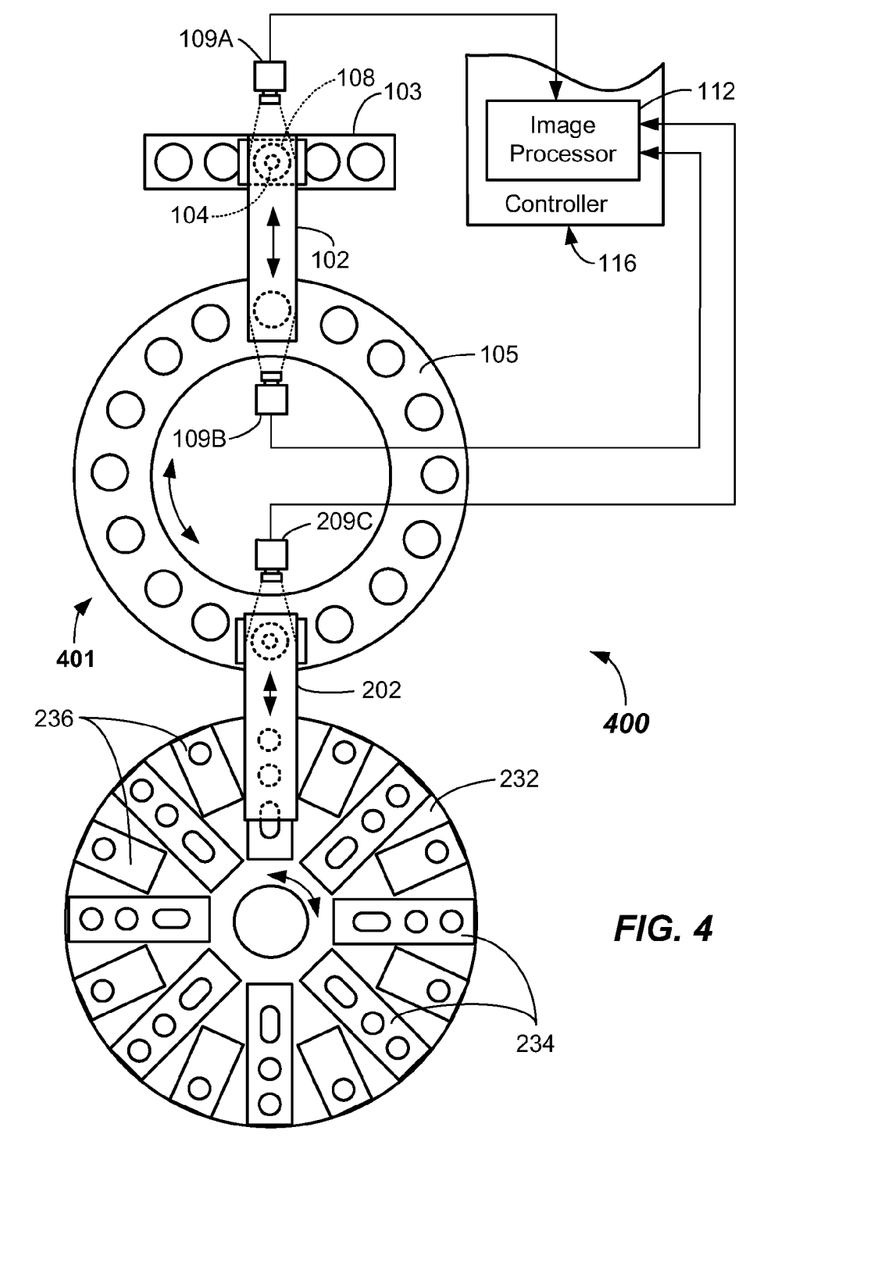
FIG. 4 illustrates a schematic top plan view of an alternative diagnostic device including an alternative liquid transfer apparatus according to embodiments.

As shown in FIG. 4, a diagnostic device 400 including a transfer apparatus 401 may include a first image capture device 109A located adjacent to a side of the first support article 103 (e.g., sample rack), and at other locations, such as adjacent to the second support article 105 (e.g., incubation ring), a second image capture devices 109B and 209C may be provided. These second image capture devices 109B and 209C monitor measure and/or verify bio-liquid specimen 108S and reagent dispense operations (e.g., reagent from of primary reagent container 234 and ancillary reagent container 236). Other suitable configurations of diagnostic devices including transfer apparatus may be used.

For example, a diagnostic device having a transfer apparatus with a single first image capture device 109A only at the side of the first support article 103 (e.g., sample rack) and adapted to measure and/or verify only specimen aspiration and/or set, measure, or verify tip immersion depth may be provided. Likewise, a diagnostic device having a transfer apparatus with a single image capture device 109B only at the side of the second support article 105 (e.g., incubation ring) and adapted to measure and/or verify only specimen dispense may be provided. In another embodiment, a diagnostic device having a transfer apparatus with a single image capture device 209C only at the side of the second support article 105 (e.g., incubation ring) and adapted to measure and/or verify only reagent dispense may be provided. Finally, a diagnostic device having a transfer apparatus with a single image capture device 209D only at the side of the second support article 105 (e.g., incubation ring) and adapted to measure and/or verify only overall assay subcomponent (e.g., specimen, reagent, and possibly diluent) addition may be provided. Any combination of the above may be provided.

For each of the embodiments discussed above, the captured image may be analyzed using a blob analysis. For example, image analysis may be performed looking at differences in digital counts within the captured image, as well as pixel locations within the images to determine edges between components. Logical group edge detection may also be used. Suitable masking, filtering and compression of the images may be used during processing, as is conventional in image processing. From this, the blob analysis may obtain various Z or other coordinates, which may be based on a priori knowledge, for determining the discussed heights, widths, calculating volumes, pipette tip location, pipette tip misalignment (laterally and/or angularly), and/or various dimensions of the bio-liquid container 108, 120, 220, and/or 220F. Color or other coding may be used to identify components (e.g., pipette tips, and bio-liquid containers 1908, 120). This may be used to ensure proper resources. At various stages, the image processor 112 may compare various images against a priori control images stored in memory to determine proper motion operation of the pipette 104, 204 and/or the first and/or second robot 102, 202. For example, instrument calibration or verification by analyzing pipette position at the image capture locations may be carried out. Repair and/or maintenance can also be triggered by analyzing the images obtained from one or more of the image capture devices 109A, 109B, 209C, 209D. Accuracy of aspiration may be improved if the diagnostic device is maintained when so indicated. Additionally, at times, one or more hardware components of the transfer apparatus 101, 301, 401 may fail prematurely. Any such failure may be captured by the various captured images, and the user alerted before too many specimens are run though a faulty diagnostic instrument. Sporadic malfunction of mechanical or hardware/firmware components in the transfer apparatus may be diagnosed. Feedback on the process may be provided at one or more steps thereof, as well as certification thereof.

According to another embodiment, the transfer apparatus 101, 301, 401 may be used to automatically determine a presence of one or more interferents (e.g., hemolysis, icterus, and/or lipemia) in the bio-liquid specimen 108S contained in the bio-liquid container 120. The presence of the interferent may be detected by the imaging processor 112 prior to being further tested by a diagnostic device 100, 300, 400 (e.g., clinical analyzer). In this manner, if the bio-liquid specimen 108S includes an interferent, additional processing, discarding, or a redraw may take place and wasted time on the diagnostic device 100, 300, 400 may be avoided. Further discussion of techniques for determining hemolysis, icterus, and/or lipemia in the bio-liquid specimen 108S may be found in U.S. Pat. Pub. 2012/0140230, assigned to the present assignee.

Figure 8:
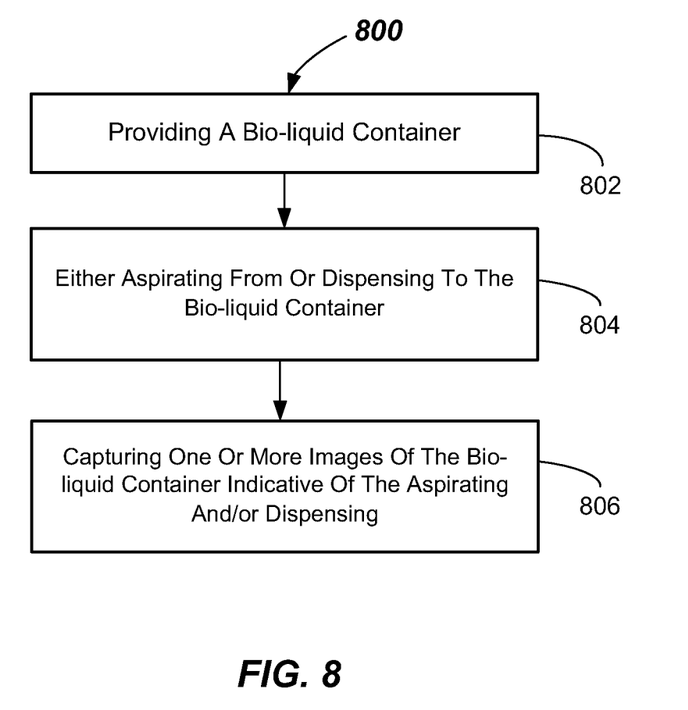
FIG. 8 illustrates a method of determining a liquid aspiration and/or liquid dispense according to embodiments.

According to one or more embodiments, a method 800 of determining an aspiration and/or dispense is provided. The method, as best shown in FIG. 8, includes, in 802, providing a bio-liquid container (e.g., bio-liquid containers 108, 120, 220, 220F, or combinations), and, in 804, either aspirating (e.g., a bio-liquid specimen 108S) from or dispensing (e.g., a specimen, liquid, semisolid, or solid reagent, or other liquid such as a diluent) to the bio-liquid container; and, in 806, capturing one or more images of the bio-liquid container indicative of the aspirating and/or dispensing. Images may be captured as discussed herein by one or more image capture devices 109A, 109B, 109C, and/or 109D (e.g., digital cameras or the like) and analyzed by the image processor 112. In some embodiments, two images, such as before and after images, are captured and analyzed to determine a change in height or volume during the aspiration and/or dispense.

Having shown the preferred embodiments, those skilled in the art will realize many variations are possible that will still be within the scope of the claimed invention. Therefore, it is the intention to limit the invention only as indicated by the scope of the claims.

What is claimed is:

1. A method of determining an aspiration and/or dispense, comprising:
   providing a bio-liquid container;
   either aspirating from or dispensing to the bio-liquid container;
   capturing an image of a pipette while the pipette is inserted into the bio-liquid container prior to the aspirating and/or dispensing from a position that is orthogonal to the pipette and the bio-liquid container; and
   capturing before and after images of the bio-liquid container indicative of the aspirating and/or dispensing.

2. The method of claim 1, comprising:
   capturing at least two images, and determining an aspirated volume based upon the at least two images.

3. The method of claim 1, comprising:
   capturing at least two images, and determining a dispensed volume based upon the at least two images.

4. The method of claim 1, comprising:
   determining whether the aspirating or the dispensing is sufficient based upon a capture of at least two images.

5. The method of claim 1, comprising:
   determining a position or orientation of the pipette based upon the image of the pipette.

6. The method of claim 1, comprising:
   determining a position of the pipette within a liquid prior to aspiration based upon the image of the pipette.

7. The method of claim 1, wherein the bio-liquid container comprises:
   a blood collection tube located in a rack, or
   a cuvette located in an incubation ring.

8. The method of claim 1, wherein the capturing of the before and after images of the bio-liquid container comprises:
   locating an image capture device adjacent to a side of a support article adapted to support the bio-liquid container.

9. The method of claim 1, wherein the capturing of the before and after images of the bio-liquid container comprises:
   capturing at least two images of the aspiration by locating an image capture device adjacent to a side of a blood collection tube residing in a sample rack, the blood collection tube comprising blood serum or plasma.

10. The method of claim 1, wherein the capturing of the before and after images of the bio-liquid container comprises:
    locating an image capture device adjacent to a side of a cuvette located in an incubation ring.

11. The method of claim 1, wherein the capturing of the before and after images of the bio-liquid container comprises:
    capturing at least two images of the dispensing at a side of a cuvette located in an incubation ring.

12. The method of claim 1, wherein the capturing of the before and after images of the bio-liquid container comprises:

locating an image capture device adjacent to a side of a cuvette at a location of reagent addition in an incubation ring.

13. The method of claim 1, wherein the capturing of the before and after images of the bio-liquid container comprises:
locating an image capture device at a location where all assay subcomponents have been added.

14. A transfer apparatus, comprising:
a support article adapted to receive a bio-liquid container; and
an image capture apparatus located adjacent to the support article and configured to capture two or more images including an image of a pipette while the pipette is inserted into the bio-liquid container from a position that is orthogonal to the pipette and the bio-liquid container and before and after images of the bio-liquid container before, during, or after either of: an aspiration, or a dispense.

15. The transfer apparatus of claim 14, wherein the image capture apparatus comprises one or more digital cameras.

16. The transfer apparatus of claim 14, wherein the image capture apparatus is located:
adjacent to a side of a sample rack, and is adapted to determine one or more changes in volume due to the aspiration;
adjacent to a side of an incubation ring, and is adapted to determine one or more changes in volume due to the dispense; and
adjacent to a side of an incubation ring, and is adapted to determine a total change in volume due to assay subcomponent additions.

17. The transfer apparatus of claim 14, comprising an image processor adapted to analyze the two or more images.

18. The transfer apparatus of claim 17, wherein the image processor is operational to determine a level of the bio-liquid before and after the aspiration.

19. The transfer apparatus of claim 17, wherein the image processor is operational to determine a level of the bio-liquid before and after the dispense.

20. A diagnostic device, comprising:
a transfer apparatus including:
a first support article adapted to receive a first bio-liquid container containing a bio-liquid;
a second support article adapted to receive a second bio-liquid container;
an image capture apparatus located adjacent to one or more of:
the first support article configured to capture two or more images including an image of a pipette while the pipette is inserted into the first bio-liquid container from a position that is orthogonal to the pipette and the bio-liquid container prior to a bio-liquid aspiration and before and after images of the first bio-liquid container at two or more points in time before, during, and after the bio-liquid aspiration,
the second support article configured to capture two or more images including before and after images of the second bio-liquid container at two or more points in time before, during, and after a bio-liquid dispense,
the second support article configured to capture two or more images including before and after images of the second bio-liquid container at two or more points in time before, during, and after a reagent dispense, and
the second support article configured to capture two or more images including before and after images of the second bio-liquid container before and after all assay subcomponent additions; and
an image processor programmed to process the images to determine at least one selected from a group of:
an aspiration height or aspiration volume,
a dispense height or dispense volume,
an overall height or volume addition,
a tip insertion depth, and
combinations thereof.

21. A method of determining an aspiration and/or dispense, comprising:
providing a bio-liquid container;
providing a pipette;
either aspirating from or dispensing to the bio-liquid container;
locating an image capture device at a location of reagent addition in an incubation ring configured to receive the bio-liquid container; and
capturing before and after images of the bio-liquid container at the reagent addition location with and without the pipette inserted into the bio-liquid container and capturing an image of the pipette while the pipette is inserted into the bio-liquid container, indicative of the aspirating and/or dispensing from a position that is orthogonal to the pipette and the bio-liquid container.

* * * * *